United States Patent [19]

Duffett

[11] Patent Number: Plant 5,322

[45] Date of Patent: Nov. 6, 1984

[54] CHRYSANTHEMUM PLANT NAMED DARING

[75] Inventor: William E. Duffett, Salinas, Calif.

[73] Assignee: Yoder Brothers, Inc., Barberton, Ohio

[21] Appl. No.: 463,921

[22] Filed: Feb. 4, 1983

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Daring having flat capitulum form; daisy capitulum type; white ray floret color; diameter across face of capitulum ranging from 90 to 105 mm. at maturity; uniform nine week photoperiodic flowering response to short days; tall plant height when grown single stem; 20 to 25 cm. peduncles on open, normally terminal sprays; and 13° C. minimum temperature tolerance for initiation and development of flowering buds.

3 Drawing Figures

The present invention comprises a new and distinct cultivar of *Chrysanthemum morifolium,* Ramat., named Daring.

Daring is a product of a planned breeding program which had the objective of creating new chrysanthemum cultivars having low temperature tolerance for cut spray mum programs with daisy capitulum type, white ray floret color, nine week flowering response, and the ability to produce commercially acceptable quality in year round programs. Such traits in combination were not present or needed improvement in previously available commercial cultivars.

Daring was originated from a cross made in a controlled breeding program in Salinas, Calif. in 1977. The female parent identified as 761334 was an unnamed white daisy seedling originated from a hybridization of Sophisticate, discloed in U.S. Plant Pat. No. 3,944, with Surfside, an unpatented cultivar. The male parent of Daring was identified as 7621401, an unnamed daisy originated from a cross between Superstar, disclosed in U.S. Plant Pat. No. 4,299, and an unnamed white anemone seedling.

Daring was discovered and selected as one flowering plant within the progeny of the stated cross by William E. Duffett in September 1978 in a controlled environment in Salinas, Calif.

The first act of asexual reproduction of Daring was accomplished when vegetative cuttings were taken from the initial selection in December 1978 in a controlled environment in Salinas, Calif. by a technician working under formulations established and supervised by William E. Duffett.

Horticultural examination of selected units initiated June 1980 has demonstrated that the combination of characteristics as herein disclosed for Daring are firmly fixed and are retained through successive generations of asexual reproduction.

Daring has not been observed under all possible environmental conditions. The phenotype may vary significantly with variations in environment such as temperature, light intensity, and day length. The following observations, measurements and comparisons describe plants grown in Salinas, Calif. and Leamington, Canada under greenhouse conditions which approximate those generally used in commercial practice.

The following traits have been repeatedly observed and are determined to be basic characteristics of Daring which in combination distinguish this chrysanthemum as a new and distinct cultivar:

(1) Flat capitulum form;

(2) Daisy capitulum type;

(3) White ray floret color;

(4) Diameter across face of capitulum ranging from 90 to 105 mm. at maturity;

(5) Uniform nine week photoperiodic flowering response to short days;

(6) Long peduncle length, ranging from 20 to 25 mm.;

(7) Tall plant height, requiring 1-2 long day weeks prior to short days to attain a flowered plant height of 80 to 100 cm. for May through October flowerings, and (8) Low temperature tolerance of 13° C. (55° F.) for initiation and development when grown in single stem cut spray programs with a continuous dark period of 13 to 14 hours.

The accompanying photographic drawings show typical inflorescence and foliage characteristics of Daring, with the colors being as nearly true as possible with illustrations of this type. Sheet 1 is a color photograph of Daring grown as a single cut spray. Sheet 2 is a black and white photograph of three views of the inflorescence of Daring. Sheet 3 is a black and white photograph showing the leaves of Daring at three stages of development (mature, intermediate and immature).

Of the many commercial cultivars known to the present inventor, the most similar in comparison to Daring is White Marble, an unpatented but commercially available cultivar. Reference is made to attached Chart A which compares certain characteritics of Daring to those same characteritics of White Marble.

Daring and White Marble are similar in ray floret color, capitulum form and type, and flowering response period. Daring has longer, stronger peduncles, larger diameter across face of capitulum, and greater plant height. Tolerance of 13° C. is similar in Daring and White Marble.

In the following description, color references are made to The Royal Horticultural Society Colour Chart. The color values were determined between 11:00 A.M. and 11:30 A.M. on Aug. 10, 1982 under 150 foot-candle light intensity at Salinas, Calif.

CLASSIFICATION

Botanical: *Chrysanthemum morifolium,* Ramat., cv Daring.

Commercial: Spray daisy cut mum.

INFLORESCENCE

Capitulum:

*Form.*—Flat.

*Type.*—Daisy.

*Diameter across face.*—90 To 105 mm.

Corolla of ray florets:

Color (*general tonality from a distance of three meters*).—White.

*Color* (*abaxial*).—155D.

*Color* (*adaxial*).—155D.

*Shape.*—Broad. Oblong with rounded tip.

Corolla of disc florets:

*Color* (*mature*).—14B.

*Color* (*immature*).—144C.

Reproductive organs:

*Androecium.*—Present disc florets only; abundant pollen.

*Gynoecium.*—Present both ray and disc florets.

PLANT

General appearance:

Height.—Tall; 80 to 100 cm. as a flowering plant from a rooted cutting, with 7 long days for May through October flowerings and maintaining a minimum nightly 13 to 14 hour continuous dark period.

Foliage:

*Color* (*abaxial*).147A.

*Color* (*adaxial*).147B.

*Shape.*—Deeply lobed and deeply serrated.

CHART A

COMPARISON OF DARING AND WHITE MARBLE

| CULTIVAR | RAY FLORET COLOR | CAPITULUM FORM AND TYPE | SPRAY FORMATION |
|---|---|---|---|
| DARING | WHITE | FLAT DAISY | TERMINAL and COMPOUND 20 to 25 cm. PEDUNCLES |
| WHITE MARBLE | WHITE | FLAT DAISY | TERMINAL and COMPOUND 15 to 20 cm. PEDUNCLES |

| CULTIVAR | DIAMETER ACROSS FACE OF CAPITULUM | PLANT HEIGHT | FLOWERING RESPONSE PERIOD |
|---|---|---|---|
| DARING | 90 to 105 mm. | 80 to 100 cm. | 9 WEEKS |
| WHITE MARBLE | 75 to 90 mm. | 70 to 80 cm. | 9 WEEKS |

COMPARISONS MADE OF PLANTS GROWN AS SINGLE STEM SPRAY CUT MUMS WITH 7 LONG DAYS IN SALINAS, CALIFORNIA

I claim:

1. A new and distinct plant of *Chrysanthemum morifolium,* Ramat., named Daring, as described and illustrated, and particularly characterized as to uniqueness by the combined characteritics of flat capitulum form; daisy capitulum type; white ray floret color; diameter across face of capitulum ranging from 90 to 105 mm. at maturity; uniform nine week flowering response; tall plant height when grown single stem; 20 to 25 cm. peduncles on open, normally terminal sprays; and 13° C. minimum temperature tolerance for initiation and development of flowering buds.

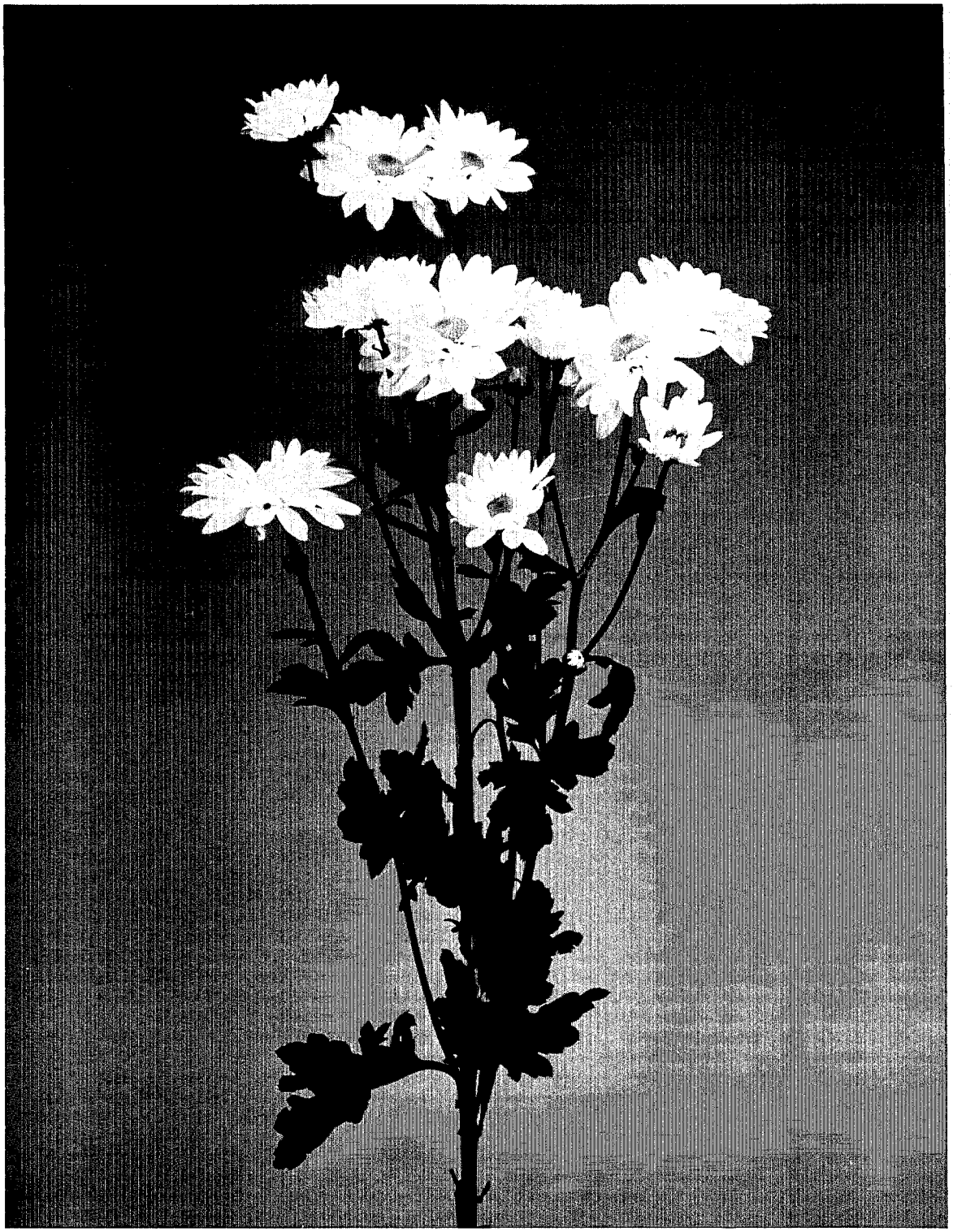

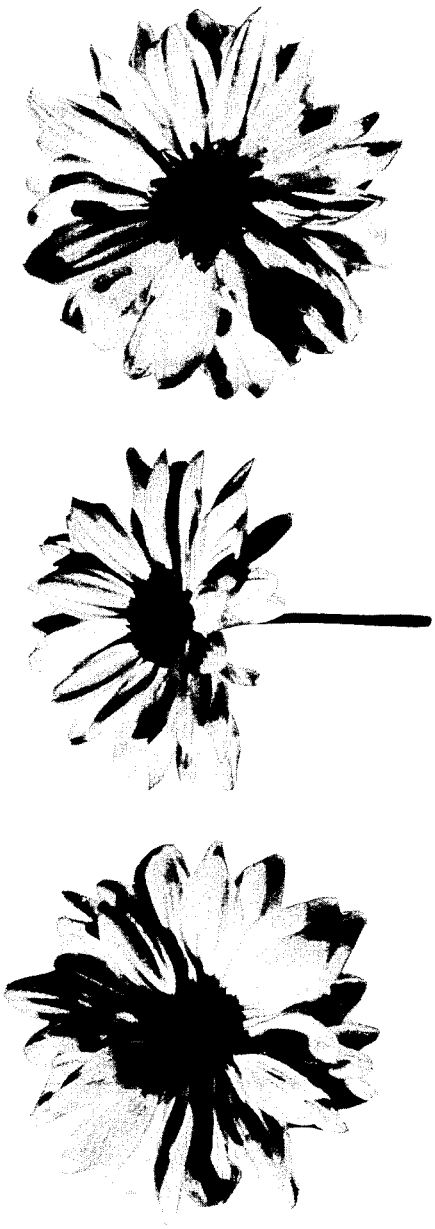

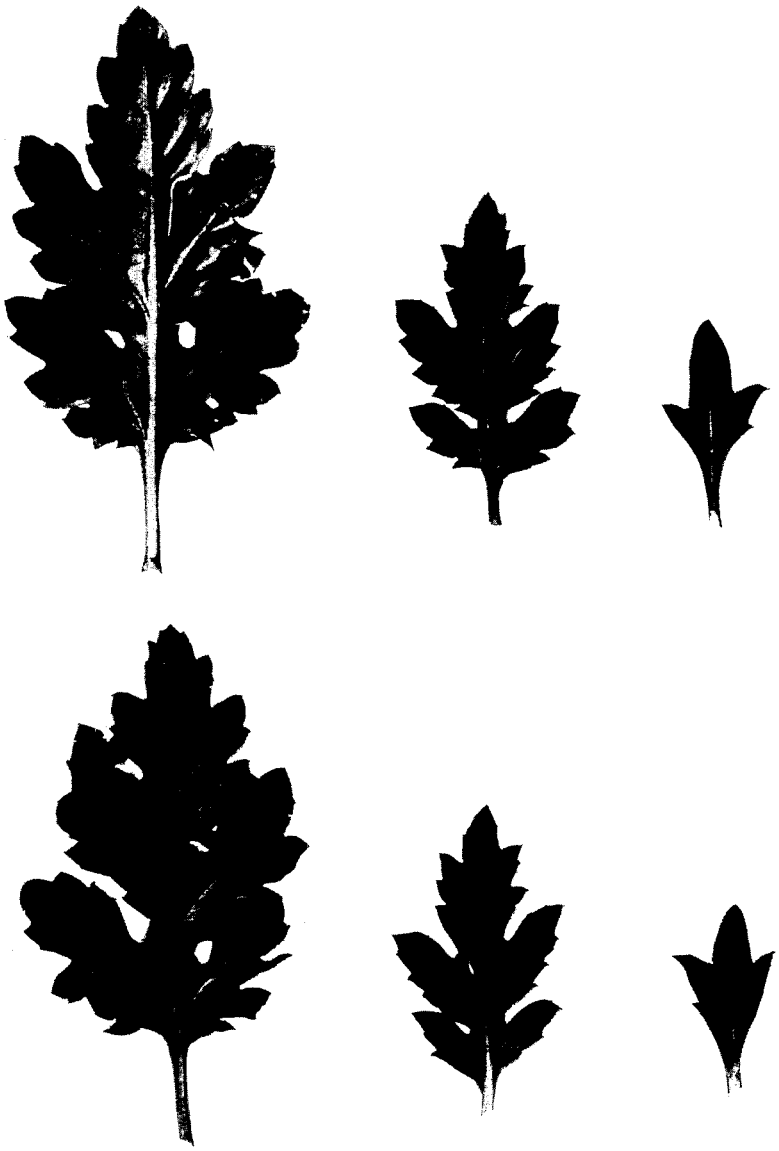

* * * * *